United States Patent
Vafi et al.

(10) Patent No.: US 6,535,576 B2
(45) Date of Patent: Mar. 18, 2003

(54) ENHANCED DIGITAL DETECTOR AND SYSTEM AND METHOD INCORPORATING SAME

(75) Inventors: Habib Vafi, Brookfield, WI (US); Scott W. Petrick, Sussex, WI (US); Douglas I. Perry, Ottawa (CA)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 153 days.

(21) Appl. No.: 09/752,084

(22) Filed: Dec. 29, 2000

(65) Prior Publication Data

US 2002/0085670 A1 Jul. 4, 2002

(51) Int. Cl.$^7$ ................................................. H05G 1/64
(52) U.S. Cl. ....................................... 378/98.8; 348/308
(58) Field of Search ........................ 378/98.8, 62, 207; 250/584, 339.02, 370.08, 370.09, 370.11, 208.1; 348/294, 302, 308

(56) References Cited

U.S. PATENT DOCUMENTS 5,970,115 A * 10/1999 Colbeth et al. ................ 378/62
6,353,654 B1 * 3/2002 Granfors et al. ............... 378/62
6,359,967 B1 * 3/2002 Bielski et al. ................. 378/62
6,470,071 B1 * 10/2002 Baertsch et al. .............. 378/62

* cited by examiner

Primary Examiner—Drew A. Dunn
Assistant Examiner—Courtney Thomas
(74) Attorney, Agent, or Firm—Fletcher, Yoder & Van Someren (57) ABSTRACT

A technique is provided for increasing the pixel pitch without increasing the interconnect density of a digital detector. Generally, a digital detector has an array of rows and columns of pixels, read out electronics and scan electronics, that are configured to generate and transmit signals based upon radiation impacting the detector. The detector also having a plurality of scan lines, which are coupled to the plurality of rows of pixels. The present technique also provides a multiplexing circuit for selectively coupling the rows of pixels to the respective scan lines for read out of the signals.

24 Claims, 5 Drawing Sheets

ENHANCED DIGITAL DETECTOR AND SYSTEM AND METHOD INCORPORATING SAME

FIELD OF THE INVENTION

The present invention relates generally to imaging systems, such as radiographic systems, and more particularly, to digital detectors. Even more particularly, the present invention relates to an apparatus and method for achieving higher pixel pitch in flat panel solid-state detector arrays.

BACKGROUND OF THE INVENTION

Digital imaging systems are becoming increasingly widespread for producing digital data, which can be reconstructed into useful radiographic images. In one application of a digital imaging system, radiation from a source is directed toward a subject, typically a patient in a medical diagnostic application, and a portion of the radiation passes through the patient and impacts a detector. The surface of the detector converts the radiation to light photons, which are sensed. The detector is divided into a matrix of discrete picture elements or pixels, and encodes output signals based upon the quantity or intensity of the radiation impacting each pixel region. Because the radiation intensity is altered as the radiation passes through the patient, the images reconstructed based upon the output signals provide a projection of the patient's tissues similar to those available through conventional photographic film techniques.

In available digital detectors, the detector surface is divided into a matrix of picture elements or pixels, with rows and columns of pixels being organized adjacent to one another to form the overall image area. When the detector is exposed to radiation, photons impact a scintillator coextensive with the image area. A series of detector elements are formed at row and column crossing points, each crossing point corresponding to a pixel making up the image matrix. In one type of detector, each element consists of a photodiode and a thin film transistor. The cathode of the diode is connected to the source of the transistor, and the anodes of all diodes are connected to a negative bias voltage. The gates of the transistors in a row are connected together and the row electrode is connected to scanning electronics. The drains of the transistors in each column are connected together and each column electrode is connected to additional readout electronics. Sequential scanning of the rows and columns permits the system to acquire the entire array or matrix of signals for subsequent signal processing and display.

In use, the signals generated at the pixel locations of the detector are sampled and digitized. The digital values are transmitted to processing circuitry where they are filtered, scaled, and further processed to produce the image data set. The data set may then be used to store the resulting image, to display the image, such as on a computer monitor, to transfer the image to conventional photographic film, and so forth. In the medical imaging field, such images are used by attending physicians and radiologists in evaluating the physical conditions of a patient and diagnosing disease and trauma.

One type of digital detector is the large area solid-state detector. Large area solid-state detector arrays provide solutions for digital imaging applications such as medical imaging, digital reproduction and non-destructive testing. As the demands on the resolution of these imaging systems increases, the requirements on the density of the interconnect also increases. The pitch of the system governs the density of the interconnect. In the art, the term "pixel pitch" typically refers to the spacing between the individual pixels. The drive to have a higher pixel pitch stretches the limits of today's interconnect technology, as well as severely impacting manufacturability, reliability and yield.

One possible solution for alleviating the interconnect density problem on digital detectors would be to move the electronics on to the panel, either as devices mounted directly to the detector array or by manufacturing the electronics as part of the panel processing. However, panel-processing technology does not yet permit on-panel construction or the necessary electronics, such as preamps and analog to digital converters that are required for panel read out. Even if such high quality devices could be designed, the additional processing costs render the approach cost prohibitive.

Mounting devices directly to the detector array through chip-on-glass construction is also an impractical solution to the interconnect density problem. The panel processing technology may not support a metal top layer, thus limiting the options for bonding the electronics to the glass. Reliability and yield of the panel itself would also be reduced in such approaches. Finally, the speed and low-noise requirements of an imaging system become problematic in such a method. The chip-on-glass method specifically affects the speed and low-noise performances by placing additional constraints on power dissipation.

There is a need, therefore, for a method to provide increased pixel pitch without impacting the density of the interconnect. It is also desirable to increase the pixel pitch without requiring changes in the panel processing technology or a solution through chip-on-glass construction.

SUMMARY OF THE INVENTION

The present invention features a digital detector system designed to respond to such needs. One aspect of the technique provides a method for acquiring signals from discrete pixels in a detector. The detector includes a matrix of rows and columns of pixels, whereby each pixel is configured to generate a signal based upon the radiation received from a radiation source. The method includes steps of commanding a multiplexer circuit to select desired rows and columns of pixels, and reading signals from the desired rows and columns.

Another aspect of the technique relates to an imaging system including a source of radiation, a control circuit to regulate the source of radiation, and a detector for receiving radiation from the source of radiation and for generating signals therefrom. The detector has an array of pixels, forming rows and columns coupled to a plurality of scan lines, each scan line being coupled to a plurality of rows of pixels. The detector has a multiplexing circuit for selectively coupling the rows of pixels to respective scan lines for read out of the signals disposed upon the detector.

Yet another aspect of the technique relates to detector comprising an array of pixels. The array of pixels forming rows and columns which are configured to generate signals based upon radiation impacting the detector. The detector also has a plurality of scan lines, wherein each scan line is coupled to a plurality of rows of pixels, and a multiplexing circuit for selectively coupling the rows of pixels to respective scan lines for read out of the signals.

DETAILED DESCRIPTION OF THE INVENTION

Figure 1:
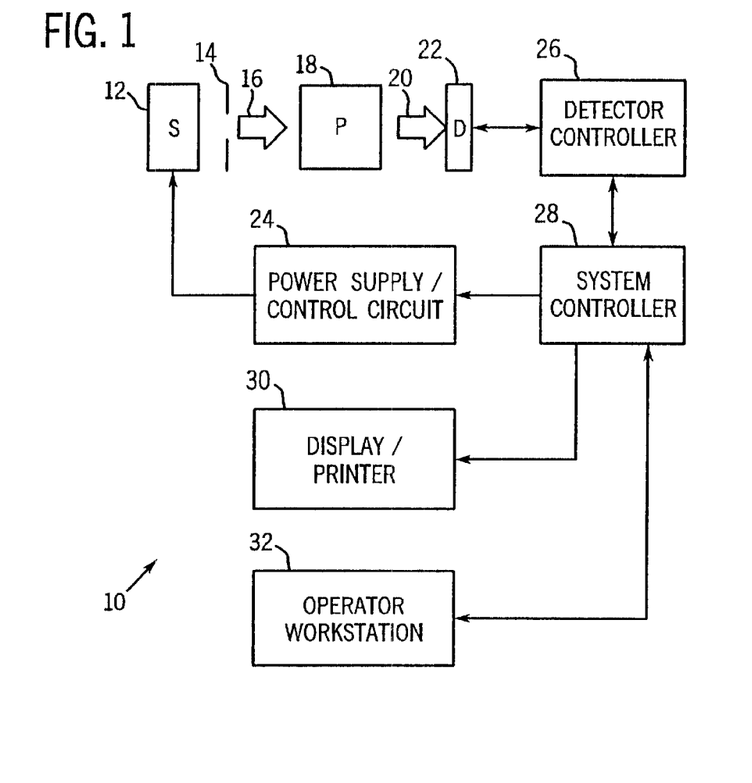
FIG. 1 is a diagrammatical overview of a digital X-ray imaging system in which the present technique is incorporated.

FIG. 1 illustrates diagrammatically an imaging system 10 for acquiring and processing discrete pixel image data. In the illustrated embodiment, system 10 is a digital X-ray system designed both to acquire original image data and to process the image data for display in accordance with the present technique. In the embodiment illustrated in FIG. 1, imaging system 10 includes a source of X-ray radiation 12 positioned adjacent to a collimator 14. Collimator 14 permits a stream of radiation 16 to pass into a region in which a subject, such as a human patient 18 is positioned. A portion of the radiation 20 passes through or around the subject and impacts a digital X-ray detector, represented generally at reference numeral 22. As described more fully below, detector 22 converts the X-ray photons received on its surface to lower energy photons, and subsequently to electric signals, which are acquired and processed to reconstruct an image of the features within the subject.

Source 12 is controlled by a power supply/control circuit 24 which furnishes both power and control signals for examination sequences. Moreover, detector 22 is coupled to a detector controller 26 which commands acquisition of the signals generated in the detector. Detector controller 26 may also execute various signal processing and filtration functions, such as for initial adjustment of dynamic ranges, interleaving of digital image data, and so forth. Both power supply/control circuit 24 and detector controller 26 are responsive to signals from a system controller 28. In general, system controller 28 commands operation of the imaging system to execute examination protocols and to process acquired image data. In the present context, system controller 28 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 28 is linked to at least one output device, such as a display or printer as indicated at reference numeral 30. The output device may include standard or special purpose computer monitors and associated processing circuitry. One or more operator workstations 32 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
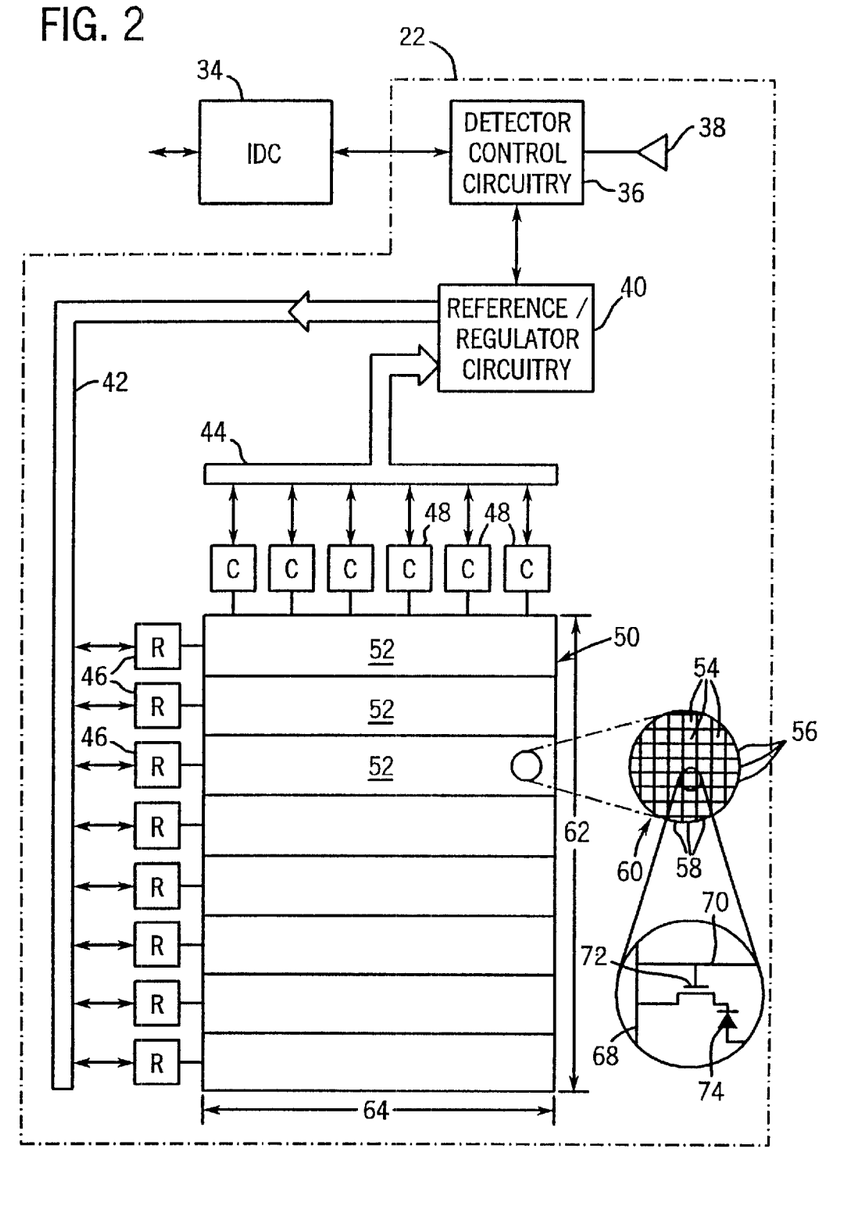
FIG. 2 is a diagrammatical representation of the functional circuitry in a detector of the system of FIG. 1 to produce image data for reconstruction.

FIG. 2 is a diagrammatical representation of functional components of digital detector 22. FIG. 2 also represents an imaging detector controller or IDC 34 which will typically be configured within detector controller 26. IDC 34 includes a CPU or digital signal processor, as well as memory circuits for commanding acquisition of sensed signals from the detector. IDC 34 is coupled via two-way fiberoptic conductors to detector control circuitry 36 within detector 22. IDC 34 thereby exchanges command signals for image data within the detector during operation.

Detector control circuitry 36 receives DC power from a power source, represented generally at reference numeral 38. Detector control circuitry 36 is configured to originate timing and control commands for row and column drivers used to transmit signals during data acquisition phases of operation of the system. Circuitry 36 therefore transmits power and control signals to reference/regulator circuitry 40, and receives digital image pixel data from circuitry 40.

In a present embodiment illustrated, detector 22 consists of a scintillator that converts X-ray photons received on the detector surface during examinations to lower energy (light) photons. An array of photodetectors then converts the light photons to electrical signals which are representative of the number of photons or the intensity of radiation impacting individual pixel regions of the detector surface. Readout electronics convert the resulting analog signals to digital values that can be processed, stored, and displayed, such as in a display 30 or a workstation 32 following reconstruction of the image. In a present form, the array of photodetectors is formed on a single base of amorphous silicon. The array elements are organized in rows and columns, with each element consisting of a photodiode and a thin film transistor. The cathode of each diode is connected to the source of the transistor, and the anodes of all diodes are connected to a negative bias voltage. The gates of the transistors in each row are connected together and the row electrodes are connected to the scanning electronics as described below. The drains of the transistors in a column are connected together and an electrode of each column is connected to readout electronics, as also described below.

In the particular embodiment illustrated in FIG. 2, by way of example, a row bus 42 includes a plurality of conductors for enabling readout from various columns of the detector, as well as for disabling rows and applying a charge compensation voltage to selected rows, where desired. A column bus 44 includes additional conductors for commanding readout from the columns while the rows are sequentially enabled. Row bus 42 is coupled to a series of row drivers 46, each of which commands enabling of a series of rows in the detector. Similarly, readout electronics 48 are coupled to column bus 44 for commanding readout of all columns of the detector. In the present technique, pixel density is enhanced by providing a greater number of pixels along row and/or column buses, with mulitplexing circuitry, for reading out pixel data.

In the illustrated embodiment, row drivers 46 and readout electronics 48 are coupled to a detector panel 50 which may be subdivided into a plurality of sections 52. Each section 52 is coupled to one of the row drivers 46, and includes a number of rows. Similarly, each column driver 48 is coupled to a series of columns. The photodiode and thin film transistor arrangement mentioned above thereby define a series of pixels or discrete picture elements 54 which are arranged in rows 56 and columns 58. The rows and columns define an image matrix 60, having a height 62 and a width 64. Again, as described below, the present technique allows an enhanced number of pixels to be read out via the row and column drivers and readout electronics.

As also illustrated in FIG. 2, each pixel 54 is generally defined at a row and column crossing, at which a column electrode 68 crosses a row electrode 70. As mentioned above, a thin film transistor 72 is provided at each crossing location for each pixel, as is a photodiode 74. As each row is enabled by row drivers 46, signals from each photodiode may be accessed via readout electronics 48, and converted to digital signals for subsequent processing and image reconstruction.

Figure 3:
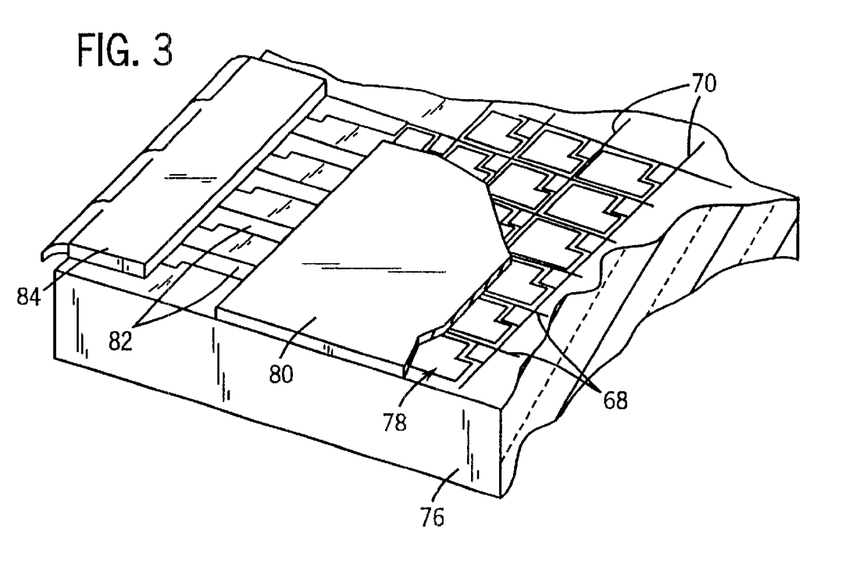
FIG. 3 is a partial sectional view illustrating an exemplary detector structure for producing the image data.

FIG. 3 generally represents an exemplary physical arrangement of the components illustrated diagrammatically in FIG. 2. As shown in FIG. 3, the detector may include a glass substrate 76 on which the components described below are disposed. Column electrodes 68 and row electrodes 70 are provided on the substrate, and an amorphous silicon flat panel array 78 is defined, including the thin film transistors and photodiodes described above. A scintillator 80 is provided over the amorphous silicon array for receiving radiation during examination sequences as described above. Contact fingers 82 are formed for communicating signals to and from the column and row electrodes, and contact leads 84 are provided for communicating the signals between the contact fingers and external circuitry.

It should be noted that the particular configuration of the detector panel 22, and the subdivision of the panel into rows and columns driven by row and column drivers is subject to various alternate configurations. In particular, more or fewer row and column drivers may be used, and detector panels having various matrix dimensions may be thereby defined. The detector panel 22 may be further subdivided into regions of multiple sections, such as along a vertical or horizontal center line.

Figure 4:
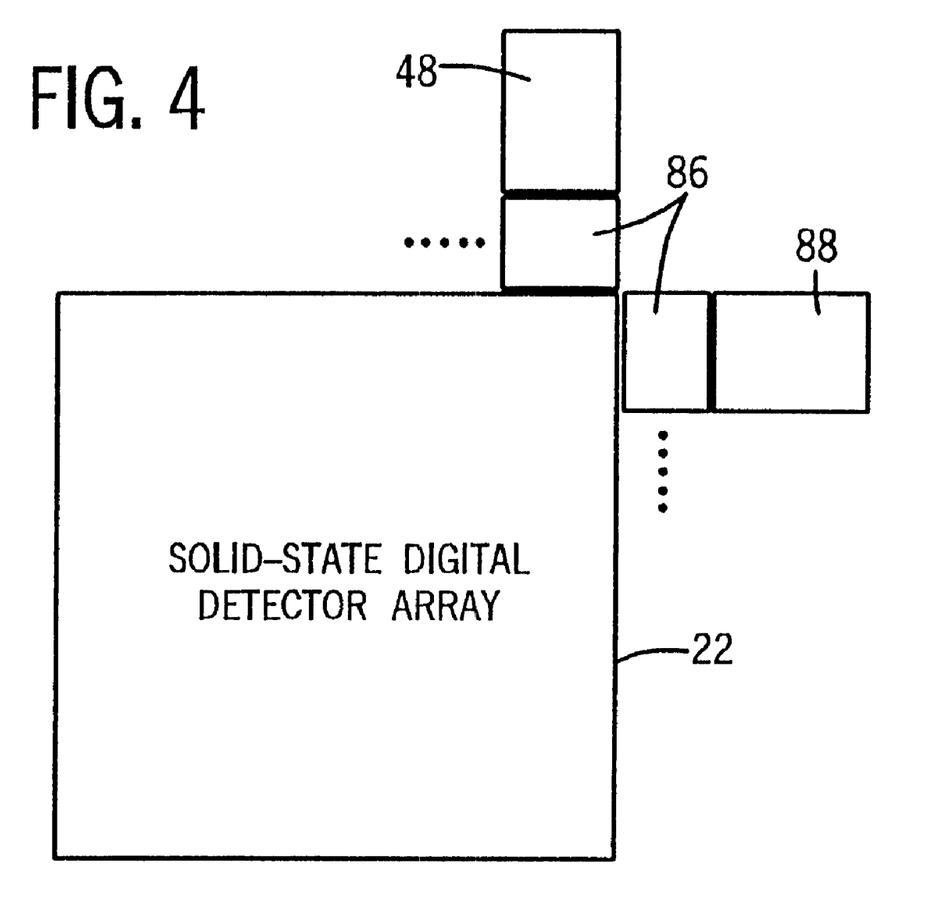
FIG. 4 is an illustration of an exemplary system architecture for the flat-panel detector.

Turning to FIG. 4, an architectural diagram is shown depicting the solid state digital detector 22 coupled to a plurality of flexible interconnects 86. The flexible interconnect 86 is coupled to readout electronics 48, and scan electronics 88. The flexible interconnect 86 provides connections to circuitry to permit the sequential scanning and reading of the individual pixels of the detector array. The readout electronics 48, as mentioned above, accommodate an analog\digital converter that digitizes charge applied to individual pixel elements during readout. The scan electronics 88 implement a scanning sequence as defined by an operator, which enables the read out of individual pixels by rows and columns. Thus, the scan electronics 88 implement a control sequence that enables the readout electronics 48.

Readout of sensed signals from the detector 22 proceeds generally as follows. Multiple scan modes may be selected for reading data from the detector 22, or for testing operability of the detector 22. In one scan mode, a single row is enabled, whereby each pixel within the row is read out. While each row is sequentially enabled for readout, column readout lines in the detector read the data from the individual pixels being scanned, thereby progressively reading out all signals from the array. Enabling begins with a start bit and moves along the series of rows in either an outside-to-inside scanning format or in an inside-to-outside format. It should be noted that in each readout mode, the readout electronics perform an analog\digital conversion of the sensed signals and the signals are then transmitted from the detector to the system controller for processing.

Figure 5:
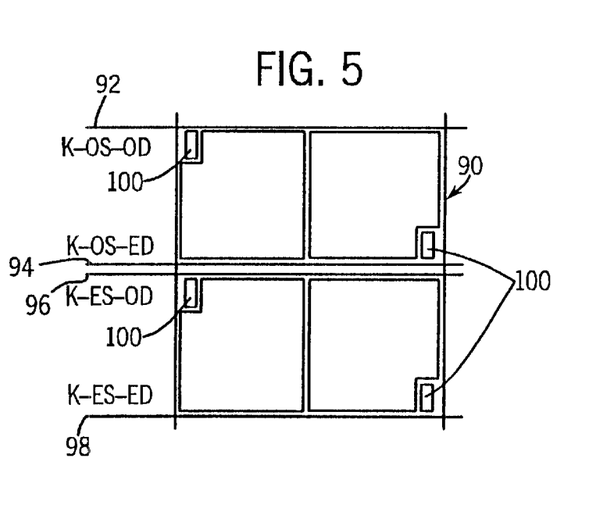
FIG. 5 is a perspective view of a pixel block illustrating scan lines and multiplexing circuits for reading signals from each independent pixel.

FIG. 5 illustrates a pixel block 90 having row lines 92, 94, 96, and 98. The detector panel, as mentioned above, is made up of a matrix of rows and columns that is scanned in one of a plurality of scan modes. Specifically, FIG. 5 illustrates two rows and two columns of pixels. Row lines 92 and 94 are illustrated being coupled to one row. Similarly, row lines 96 and 98 are shown coupled to the second row. Thus, four pixels are shown, wherein row lines 92 and 94 scan the first row, and row lines 96 and 98 scan the second row. Readout occurs as one mode is selected and an operator initiates a scan enabling a row line to scan the pixels within that row, whereby the image data is read by a column readout line. Additionally, field effect transistors 100 are illustrated disposed within each pixel, corresponding to the thin film transistors discussed above.

Figure 6:
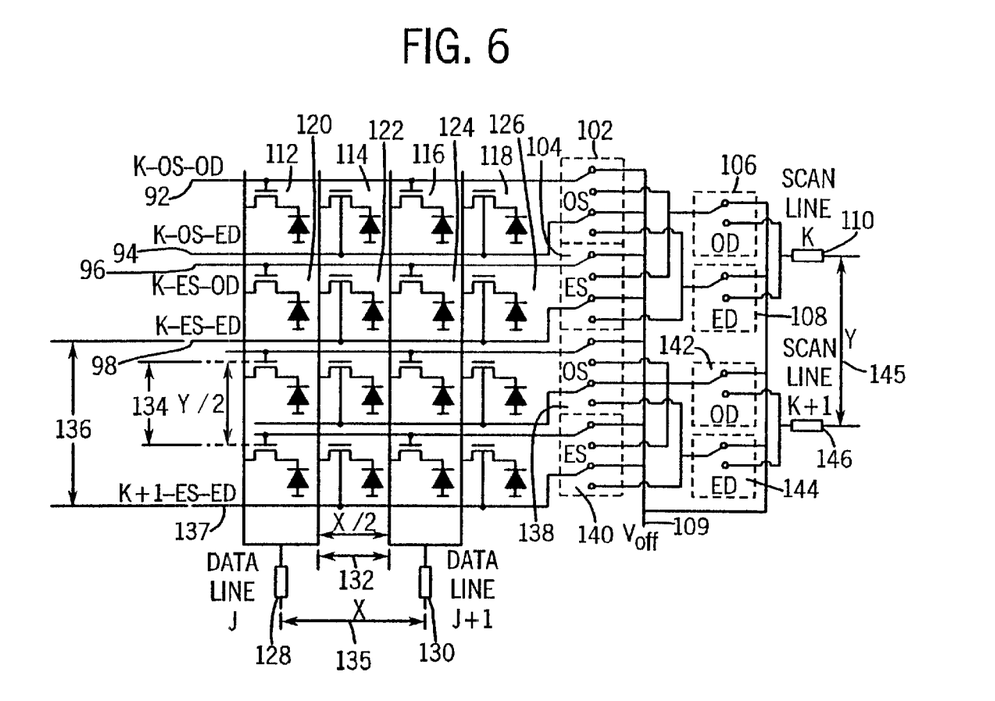
FIG. 6 is an illustration of an exemplary architectural design of a detector array with increased pixel pitch.

FIG. 6 represents, in somewhat greater detail, the individual pixels and the multiplexing circuitry utilized to increase pixel pitch without increasing the interconnect density. In the illustrated embodiment, each row of pixels is connected to a row line 92, 94, 96, and 98. Specifically, each row of pixels is coupled to two row lines. Further, each row line is coupled to a multiplexer having solid state switches, such as field effect transistors for selective row enabling. For instance, row lines 92 and 94 are coupled to a switch set 102, and row line 96 and 98 are coupled to switch set 104. In turn, switch set 102 is coupled to switches 106 and 108. Similarly, switch set 104 is also coupled to switches 106 and 108. A voltage source 109 is provided for disabling the pixels in the matrix via the switches. It should be noted that this embodiment illustrates only one scanning arrangement and approach. However, different approaches may be used for similar results and based upon the present technique. For example, in this particular embodiment, two row lines are coupled to alternate pixels within the same row, and the row lines are coupled to two individual switches within the same multiplexing sets operated to scan that particular row. In addition, the first set of switches, when enabled, selects the column of pixels being scanned, whereas the second set of switches enables the particular row of pixels being scanned. It should be noted that a different scanning mode may be implemented, whereby a different sequencing scheme of scanning pixels for readout may be established.

As mentioned above, each row line is coupled to alternate pixels within the same row. Consequently, row lines 92 and 94 are configured to scan the same row. For instance, row line 92 is coupled to pixels 112 and 116. Row line 94 is coupled to pixels 114 and 118. Thus, row line 92 enables a scan of pixels 112 and 116 when scan line 110 is enabled and a logical high input signal is applied to switch 102 and 106 as described in greater detail below. Similarly, in the next row, row line 96 is coupled to pixels 120 and 124, and row line 98 is coupled to pixels 122 and 126. As the specific row line is enabled, which is accomplished by enabling scan line 110, the individual pixels will be scanned and read out by column read out lines 128 and 130. Although the individual row lines are coupled to specific pixels, the column readout lines are coupled to every pixel within that column in the present embodiment. However, it should be understood that the column readout lines may be coupled to columns in a manner similar to the row lines, whereby alternate pixels may be coupled to each column readout line.

The pixel length, by row and column, is shown in FIG. 6 by reference numeral 132 and 134 respectively. Additionally, in this embodiment, row line 137 is depicted coupled to a series of pixels, and to a switch 140. Switch 140 is then coupled to switches 142 and 144. Switches 140, 142, 144 are enabled by scan line 146. As mentioned above, the row lines are enabled when the appropriate switches and the scan line are enabled, thus allowing the read out to occur via column readout lines 128 and 130.

A feature of the present embodiment is that column readout lines 128 and 130 are connected to a single readout channel. Thus, the present embodiment provides two scan lines to activate either column readout line 128 or column readout line 130. Therefore, readout is performed twice for each row in a complete, or maximum resolution scan. For instance, each row is scanned twice, for example row lines 92 and 94, when enabled allow the scanning of the first row. Row line 92 will enable the individual pixels coupled to it and row line 94 will enable the alternate pixels for readout. Furthermore, connected column readout lines are coupled to every pixel within the column, thus reading all the enabled pixels during progressive enabling of the pixels of each row.

Pixel pitch, as mentioned above, is determined by the spacing between the individual pixels given as X/2 by Y/2 represented by reference numerals 132 and 134 in FIG. 6. The distance between the connected column readout lines may be referred to as X as referenced by numeral 135. Similarly, the distance between scan lines 110 and 146 may be referred to as Y as referenced by numeral 145. As mentioned above, pixel pitch is the distance between the pixels. While conventional arrangements would provide a pitch of X×Y, the present technique applied in this illustrated example provides an enhanced pitch of X/2×Y/2.

Figure 7:
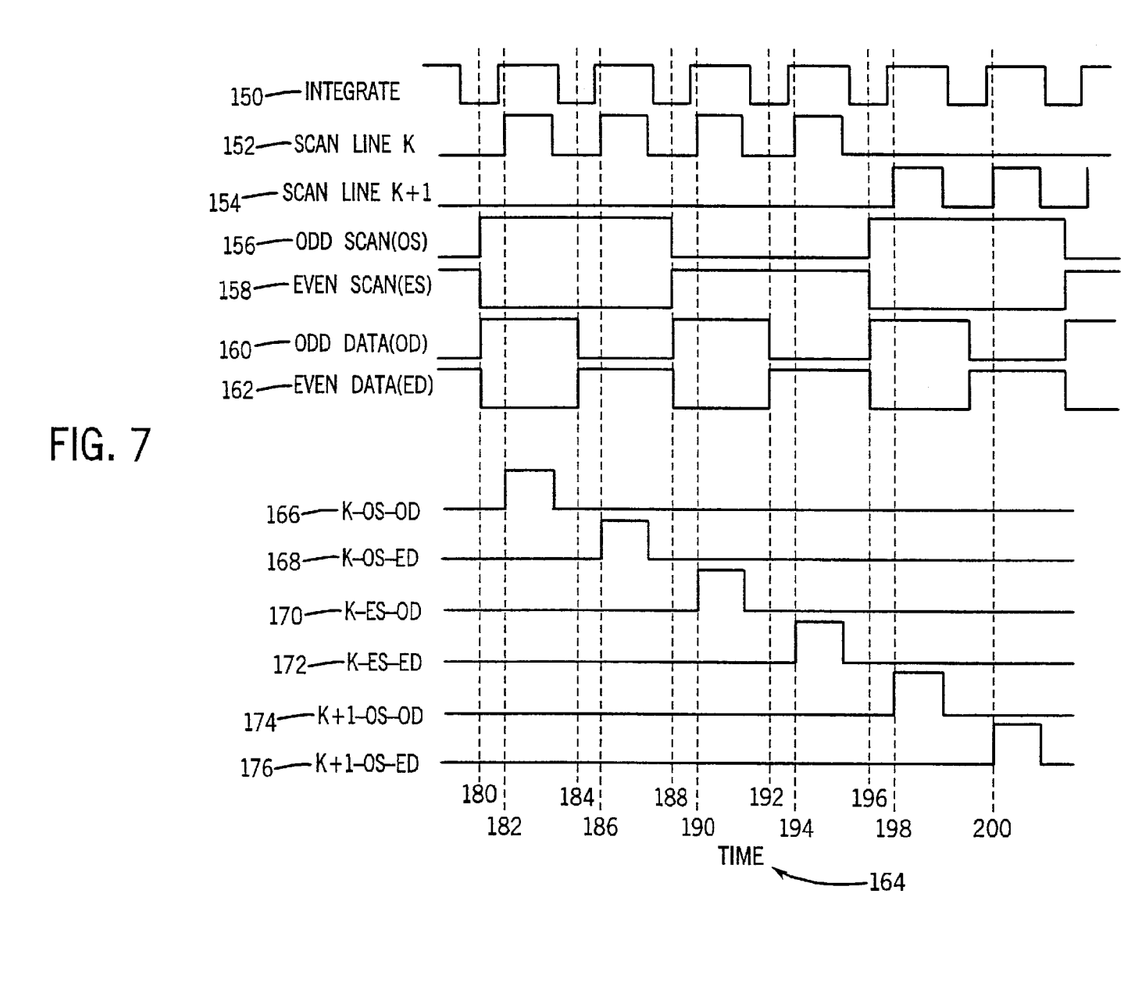
FIG. 7 is an operational sequence diagram illustrating the logical states for an exemplary architectural design of a detector array.

Timing and control sequencing for selectively scanning the arrangement of FIG. 6 is described more fully in FIG. 7. FIG. 7 graphically represents the pulse signals applied to the solid state switches shown in FIG. 6 during the course of scanning a detector. Particularly, FIG. 7 illustrates the logical states of the row lines and switches at given times. The y-axes of the traces represent the logical signal levels for input to the switches and row lines, displayed as an integrated sequence 150, a scan line sequence 152, a scan line sequence 154, and sequencing 156 for odd scan switches, sequencing 158 for even scan switches, sequencing 160 for odd data switches, and sequencing 162 for even data switches. The x-axis 164 represents the time, with specific times of interest labeled, from time 180 to time 200.

The integrated pulse signal trace 150 indicates a series of pulses that enable the scanning of rows of pixels. The pulse signal trace 152 represents the logical state of scan line 110. Similarly, the pulse signal trace 154 represents the logic state of scan line 146. The states of inputs to switches 102 and 104 are represented by pulse signal traces 156 and 158, with a logical high placing the switch in a conductive state (i.e., in communication with the scan line). Additionally, the states of inputs to switches 106 and 108 are represented by input signal traces 160 and 162. Logical states of row lines 92, 94, 96 and 98 are represented by input signal traces 166, 168, 170 and 172. Logical states of additional row lines K+1-OS-OD and K+1-OS-ED (not shown in FIG. 6) are represented by pulse signal traces 174 and 176.

As will be appreciated by those skilled in the art, when a logical "low" signal is shown, the respective switch is nonconductive. Furthermore, when a logical "high" signal is shown, the switch is enabled to scan pixels in a row of pixels when a corresponding scan line is enabled. For instance, at time 180, the pulse signal of scan line 110 (FIG. 6) is at a logical low as referenced by pulse signal trace 152. Also, at time 180, inputs to switches 102 and 106 are placed at a logical high pulse signal, as shown in traces 156 and 160, respectively. Additionally, at time 180 inputs to switches 104 and 108 are at a logical low as referenced by traces 158 and 162. Thus, when scan line 110 is enabled, column readout lines 128 and 130 read the image data from pixels 112 and 116, respectively. Thus, at time 182 switches 102 and 106 remain conductive, and scan line 110 is enabled, whereby row line 92 is enabled and pixels 112 and 116 are read by column readout lines 128 and 130 as shown in FIG. 6. The logical high input signal on trace 152 represents the enabling of row line 92. Looking further at FIG. 7, switches 102 and 106 (FIG. 6) receive a logical high input signal as indicated by traces 156 and 160 at time 180, and remain at that logical state until time 188. The logical states of switches 104 and 108, as indicated by traces 158 and 162 are low at time 180 and, therefore, the switches remain nonconductive.

At time 184 scan line 110 is not enabled, and the row of pixels is not scanned for readout. Input for scan line 110 is thus shown at a logical low, as referenced by trace 152. However, switch 102 remains enabled, as indicated by the logical high input signal on trace 156. Switch 104 remains nonconductive, as represented by a logical low input on trace 158. Although switches 102 and 104 remain at their same logical states from time 180, switches 106 and 108 are nonconductive and conductive, respectively. That is, switch 106 receives a logical low input, as illustrated by the logical low pulse signal on trace 160. Switch 108 is enabled at time 184 and its input remains at logical high state until time 188. Readout of row line 94 occurs at time 186 when scan line 110 is enabled, as illustrated by the input signal on trace 168. Thus, the only event occurring at time 186 is the scan line 110 being enabled, whereby readout of row line 94 occurs. Readout occurs similarly to that described for row line 92, wherein column readout lines 128 and 130 read the selected pixels. Specifically, row line 94 enables the scan of pixels 114 and 118. Thus, row line 92 enables the scan of pixels 114 and 118 as indicated by the logical high input on trace 152 at time 186.

Referring to time 188, scan line 110 is not enabled, as indicated by the logical low input signal on trace 152. However, scanning is completed for row line 94, with pixels 112, 114, 116, 118, and all other pixels in the row having been read out. At time 188, although the scan line 110 is not enabled, switches 104 and 106 become enabled as indicated by traces 158 and 160, respectively in FIG. 7, and switches 102 and 108 are disabled as indicated by the logical low input on traces 156 and 162. Subsequently, at time 190 scan line 110 is enabled as shown by the logical high input signal on trace 152. Switch 102 remains nonconductive, having a logical low input signal, and switch 104 remains conductive. Switch 106 also remains conductive as indicated by the logical high input signal on trace 160. However, switch 108 remains nonconductive. Because scan line 110 is enabled and switches 104 and 106 are conductive, row line 96 is scanned as illustrated by the logical high input signal on trace 170. Thus, pixels 120 and 124 are read out through column readout lines 128 and 130, respectively. At time 192, scan line 110 is disabled as shown by the logical low input signal on trace 152. At the same time, switch 108 is enabled, and switch 106 is disabled. The corresponding logical high and low input signals are indicated on traces 160 and 162 at time 192. At the same time, switches 102 and 104 remain at their operative states, that is, switch 102 remains nonconductive whereas switch 104 is conductive as shown by traces 156 and 158.

At time 194, scan line 110 is enabled as illustrated by the input signal trace 152 at a logical high. Switches 102 and 104 remain at their respective states from time 192. Switch 106 is also nonconductive as indicated by the logical low input signal on trace 160. However, switch 108 remains conductive as indicated by the logical high input signal on trace 162. Because switches 104 and 108 are conductive, row line 98 is enabled once scan line 110 is enabled. Thus, at time 194, scan line 110 is enabled whereby line 98 is enabled, providing data to column readout lines 128 and 130. Trace 172 in FIG. 7 indicates the logical high signal at which scan line 98 is enabled. When the row 98 is scanned at time 194, pixel data from pixels 122 and 126 are read out via column readout lines 128 and 130, respectively.

At time 196, scan line 110 not enabled as illustrated by a logical low input signal on trace 152, but switches 102 and 106 are enabled as indicated by the logical high input signals on traces 156 and 160. At the same time, switches 104 and 108 are made nonconductive, as shown by the logical low input signal on traces 158 and 162. At time 198, scan line 146 is enabled and permits scanning, while scan line 110 remains inactive. As scan line 146 is enabled, as indicated by the signal on trace 154 and switches 102 and 106 are maintained conductive, as indicated by the logical high input signals on traces 156 and 160, a scan of row line K+1-OS-OD is enabled, as illustrated by the logical high input signal on trace 174. Image data is thus retrieved by the column readout lines 128 and 130. At time 200 scan line 146 is again enabled until the scan of all pixels coupled to the row lines enabled by scan line 146 is completed. It should be noted that the pulse signals for switches 138, 140, 142 and 144 operate similarly to switches 102, 104, 106, and 108. In this manner, data from all rows and columns is read through sequential switching of the multiplexing circuitry.

It should be noted that the multiplexing circuitry includes switches on the detector to control scanning. Additionally, any type of suitable switching mechanism may be employed for this purpose. In particular, any multiplexing system permitting readout and allowing the pixel pitch to be increased, preferably without impacting the interconnect density may be applied. It should also be noted that the data and scan multiplexers may be exchanged. For example, switches enabling different readout modes by manipulating column readout lines may also be applied, with switches being enabled for different modes of readout from the pixels. Also, multiplexers capable of enabling all pixels simultaneously within a row line or in a sequential pattern may be provided. Additionally, the present embodiment illustrates switches formed or placed on the detector, however it should be noted that the switching mechanism may be located at a position other than the detector panel. Furthermore, multiple scanning modes may be implemented, such as to scan each individual pixel for maximum resolution or groups of pixels for enhanced speed.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A detector for an imaging system comprising:
   an array of pixels forming rows and columns, and configured to generate signals based upon radiation impacting the detector;
   a plurality of scan lines, each scan line being adapted to be coupled to a plurality of rows of pixels; and
   a multiplexing circuit for selectively coupling the rows of pixels to respective scan lines for read out of the signals.

2. The detector as in claim 1, further comprising a plurality of column readout lines coupled to a plurality of columns of pixels.

3. The detector as in claim 2, wherein each column readout line is coupled to two columns of pixels.

4. The detector as in claim 1, wherein the multiplexing circuit includes a first set of switches for selecting rows of pixels for readout.

5. The detector as in claim 1, wherein the multiplexing circuit includes a second set of switches for selecting columns of pixels for readout.

6. The detector as in claim 1, wherein each scan line is coupled to two rows of pixels.

7. The detector as in claim 1, wherein the detector includes a plurality of column readout lines coupled to the pixels, and wherein the number of pixels is at least two times the sum of the number of scan lines and column readout lines.

8. The detector as in claim 1, further comprising a control circuit to regulate switching of the multiplexer circuit.

9. The detector as in claim 1, wherein each of the pixels includes a thin film transistor and a photodiode.

10. A digital imaging system, comprising:
    a source of radiation;
    a control circuit to regulate the source of radiation; and
    a detector for receiving radiation from the source of radiation and for generating signals therefrom, the detector having an array of pixels forming rows and columns, and a plurality of scan lines, each scan line being adapted to be coupled to a plurality of rows of pixels, and a mulitplexing circuit for selectively coupling the rows of pixels to respective scan lines for read out of the signals.

11. The system as in claim 10, further comprising a plurality of column readout lines coupled to a plurality of column of pixels.

12. The system as in claim 10, wherein each column readout line is coupled to two columns of pixels.

13. The system as in claim 10, wherein the multiplexing circuit includes a first set of switches for selecting rows of pixels for readout.

14. The system as in claim 10, wherein the multiplexing circuit includes a second set of switches for selecting columns of pixels for readout.

15. The system as in claim 10, wherein each scan line is coupled to two rows of pixels.

16. The system as in claim 10, wherein the system includes a plurality of column readout lines coupled to the pixels, and wherein the number of pixels is at least two times the sum of the number of scan lines and column readout lines.

17. The system as in claim 10, further comprising a control circuit to regulate switching of the multiplexer circuit.

18. The system as in claim 10, wherein each of the pixels includes a thin film transistor and a photodiode.

19. The system as in claim 10, wherein the source of radiation is an x-ray source.

20. The system as in claim 10, further comprising data acquisition circuitry for receiving signals generated by the detector and reconstructing useful images based thereon.

21. A method for acquiring signals from discrete pixels in a detector, the detector including a matrix of rows and columns of pixels, each pixel configured to generate a signal based upon radiation received, the method comprising:

commanding a multiplexer circuit to selectively couple desired pixels of the rows and columns of pixels to enabling scan lines;

reading signals from the pixels of the desired rows and columns.

22. The method as recited in claim 21, wherein each of the scan lines is adapted for coupling to a plurality of rows of pixels via the multiplexing circuit.

23. The method as recited in claim 21, wherein the step of commanding a multiplexing circuit includes commanding a first multiplexing circuit for coupling pixels of each scan line to desired columns of pixels for read out.

24. The method as in claim 21, wherein the step of reading the signals from the pixels includes reading signals from one of a plurality of a columns of pixels coupled to a respective column of readout lines.

* * * * *